(12) United States Patent
Kim et al.

(10) Patent No.: US 10,617,760 B2
(45) Date of Patent: Apr. 14, 2020

(54) COMPOSITION FOR TARGET-SPECIFIC PHOTOTHERMAL THERAPY

(71) Applicant: GACHON UNIVERSITY OF INDUSTRY-ACADEMIC COOPERATION FOUNDATION, Gyeonggi-do (KR)

(72) Inventors: Woo Jae Kim, Seoul (KR); Jo-Eun Um, Seoul (KR)

(73) Assignee: GACHON UNIVERSITY OF INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 39 days.

(21) Appl. No.: 15/558,308

(22) PCT Filed: Feb. 12, 2016

(86) PCT No.: PCT/KR2016/001439
§ 371 (c)(1),
(2) Date: Jan. 22, 2018

(87) PCT Pub. No.: WO2016/148402
PCT Pub. Date: Sep. 22, 2016

(65) Prior Publication Data
US 2018/0133317 A1    May 17, 2018

(30) Foreign Application Priority Data

Mar. 14, 2015  (KR) .................. 10-2015-0035430

(51) Int. Cl.
| | | |
|---|---|---|
| A61K 41/00 | (2020.01) |
| A61K 47/36 | (2006.01) |
| A61K 33/44 | (2006.01) |
| A61K 9/00 | (2006.01) |
| A61K 47/02 | (2006.01) |
| A61K 49/00 | (2006.01) |
| A61P 17/06 | (2006.01) |
| A61P 9/10 | (2006.01) |
| A61P 25/28 | (2006.01) |
| A61P 37/06 | (2006.01) |
| A61P 19/02 | (2006.01) |
| A61P 1/00 | (2006.01) |
| A61P 11/00 | (2006.01) |
| A61P 19/08 | (2006.01) |
| A61P 29/00 | (2006.01) |
| A61B 5/00 | (2006.01) |
| A61K 9/20 | (2006.01) |
| A61N 5/06 | (2006.01) |
| A61N 5/067 | (2006.01) |

(52) U.S. Cl.
CPC ........ *A61K 41/0052* (2013.01); *A61B 5/0059* (2013.01); *A61K 9/0009* (2013.01); *A61K 9/0019* (2013.01); *A61K 9/0053* (2013.01); *A61K 9/0092* (2013.01); *A61K 9/2059* (2013.01); *A61K 33/44* (2013.01); *A61K 47/02* (2013.01); *A61K 47/36* (2013.01); *A61K 49/0065* (2013.01); *A61N 5/062* (2013.01); *A61P 1/00* (2018.01); *A61P 9/10* (2018.01); *A61P 11/00* (2018.01); *A61P 17/06* (2018.01); *A61P 19/02* (2018.01); *A61P 19/08* (2018.01); *A61P 25/28* (2018.01); *A61P 29/00* (2018.01); *A61P 37/06* (2018.01); *A61N 2005/067* (2013.01); *A61N 2005/0659* (2013.01)

(58) Field of Classification Search
None
See application file for complete search history.

(56) References Cited

U.S. PATENT DOCUMENTS

| | | | |
|---|---|---|---|
| 2004/0068207 A1 | 4/2004 | Tabata |
| 2008/0227687 A1 | 9/2008 | Harrison et al. |

FOREIGN PATENT DOCUMENTS

| | | |
|---|---|---|
| KR | 10-2012-0124611 A | 11/2012 |
| KR | 10-2014-0014443 A | 2/2014 |

OTHER PUBLICATIONS

Kosuge et al. "Near Infrared Imaging and Photothermal Ablation of Vascular Inflammation Using Single-Walled Carbon Nanotubes", J Am Heart Assoc. Dec. 2012; 1(6) (Year: 2012).*
Kotagiri, Nalinikanth, et al "Selective Pathogen Targeting and Macrophage Evading Carbon Nanotubes Through Dextran Sulfate Coating and PEGylation for Photothermal Theranostics" Journal of Biomedical Nanotechnology, 2013, vol. 9, No. 6, pp. 1008-1016.

* cited by examiner

*Primary Examiner* — James W Rogers
(74) *Attorney, Agent, or Firm* — Nath, Goldberg & Meyer; Joshua B. Goldberg; Stephanie Majkut

(57) ABSTRACT

Provided are a composition for target-specific photothermal therapy and a method of photothermal therapy using the composition and more particularly, a method of photothermal therapy for selectively killing inflammatory cells by using the composition for target-specific photothermal therapy comprising carbon nanotubes coated with dextran. According to the present invention, the composition for photothermal therapy comprising the carbon nanotubes coated with dextran is absorbed only into desired target cells, i.e., inflammatory cells, and causes thermotherapeutic action through light irradiated from an external light source, while not damaging cells except for inflammatory cells. The method of photothermal therapy using the composition for photothermal therapy has advantages of minimizing side effects and maximizing therapeutic effects.

3 Claims, 7 Drawing Sheets

COMPOSITION FOR TARGET-SPECIFIC PHOTOTHERMAL THERAPY

This is a National Phase Application filed under 35 U.S.C. 371 as a national stage of PCT/KR2016/001439, filed Feb. 12, 2016, an application claiming the benefit of Korean Application No. KPA10-2015-0035430, filed Mar. 14, 2015, the content of each of which is hereby incorporated by reference in its entirety.

BACKGROUND OF THE INVENTION

Field of the Invention

The present invention relates to a composition for target-specific photothermal therapy and a method of photothermal therapy using the composition. More specifically, the present invention relates to a method of photothermal therapy for selectively killing inflammatory cells by using the composition for target-specific photothermal therapy comprising carbon nanotubes coated with dextran.

According to the present invention, the composition for photothermal therapy comprising the carbon nanotubes coated with dextran is absorbed only into desired target cells, i.e., inflammatory cells, and causes thermotherapeutic action through light irradiated from an external light source, while not damaging cells except for inflammatory cells. The method of photothermal therapy using the composition for photothermal therapy has advantages of minimizing side effects and maximizing therapeutic effects.

Related Art

Photothermal therapy is a therapy method of accumulating a material generating heat by absorbing light in a near infrared area in a location requiring hyperthermal therapy, and by irradiating light (infrared rays, etc.). Since the absorption of the light in the near infrared area is very low in the body tissue, a depth for local therapy in the body is increased, thereby minimizing damage on other tissues except for the location where the material is accumulated.

Currently, it has been reported that most of materials studied for photothermal therapy are nanoparticles having sizes of 20 to 300 nm, in which the size range has high permeability and therapeutic effects of the particles on tumor tissues. When the tumor is grown, angiogenesis is required, and blood vessels formed as such have some different features from general blood vessels, such as causing leakage due to low and loose lymphatic ejection and the like. Due to these characteristics, methods in which therapeutic particles are relatively accumulated in cancer cells compared to other sites, and in addition, target cells (e.g., antibodies) are actively selected have been studied.

As examples for near-infrared photothermal therapy of cancer in a living body using a photothermal material, cases using gold nanorods made of metal and inorganic nano materials [Non-Patent Document 1: E. B. Dickerson et al., Cancer Letters 269:57-66 (2008)], gold nanoshells [Non-Patent Document 2: D. P. O'Neal et al., Cancer Letters 209:171-176 (2004) and Non-Patent Document 3: A. M. Gobin et al., Nano Letters 7:1929-1934 (2007)], carbon nanotubes [Non-Patent Document 4: S Ghoshy et al., ACS Nano 3:2667-2673 (2009) and Non-Patent Document 5: H. K. Moon et al., ACS Nano 3:3707-3713 (2009)] and indocyanine green as an organic dye [Non-Patent Document 6: W. R. Chen et al., Cancer Letters 94:125-131 (1995), Non-Patent Document 7: W. R. Chen et al., Cancer Letters 98:169-173 (1996), and Non-Patent Document 8: W. R. Chen et al., Cancer Letters 115:25-30 (1997)] have been reported.

SUMMARY OF THE INVENTION

The present inventors made many efforts to develop a composition for target-specific photothermal therapy which has an effect only on cells to be treated without damaging other cells, and as a result, verified that the composition may selectively kill only the cells to be treated by using carbon nanotubes coated with dextran.

An exemplary embodiment of the present invention provides a composition for target-specific photothermal therapy comprising: (a) carbon nanotubes; and (b) dextran coated on the surface of the carbon nanotubes.

The target may be inflammatory cells.

The composition for photothermal therapy may be used for diagnosis or treatment of inflammatory cell-mediated diseases.

The inflammatory cell-mediated disease may include rheumatoid arthritis, ulcerative colitis, Crohn's disease, psoriasis, osteomyelitis, multiple sclerosis, atherosclerosis, pulmonary fibrosis, sarcoidosis (sarcomatosis), systemic sclerosis, graft versus host disease (GVHD) or chronic inflammation.

The carbon nanotubes may be single-walled carbon nanotubes (SWNTs).

Another exemplary embodiment of the present invention provides a method of photothermal therapy for subjects except for the human, comprising: administering a composition for target-specific photothermal therapy according to the present invention; and irradiating light.

In the administering of the composition for target-specific photothermal therapy, the composition for target-specific photothermal therapy according to the present invention may be administered with an amount of 0.05 mg/ml.

The light may be a near infrared (NIR) laser having a wavelength of 600 to 1000 nm.

The composition for photothermal therapy may be used for diagnosis or treatment of inflammatory cell-mediated diseases.

The inflammatory cell-mediated disease may include rheumatoid arthritis, ulcerative colitis, Crohn's disease, psoriasis, osteomyelitis, multiple sclerosis, atherosclerosis, pulmonary fibrosis, sarcoidosis (sarcomatosis), systemic sclerosis, graft versus host disease (GVHD) or chronic inflammation.

According to the present invention, the composition for photothermal therapy comprising carbon nanotubes coated with dextran is absorbed only into desired target cells, i.e., inflammatory cells to cause thermotherapeutic action through light irradiated from an external light source, while not damaging cells except for inflammatory cells. Accordingly, the composition for photothermal therapy has advantages of minimizing side effects and maximizing therapeutic effects.

DESCRIPTION OF EXEMPLARY EMBODIMENTS

Figure 1:
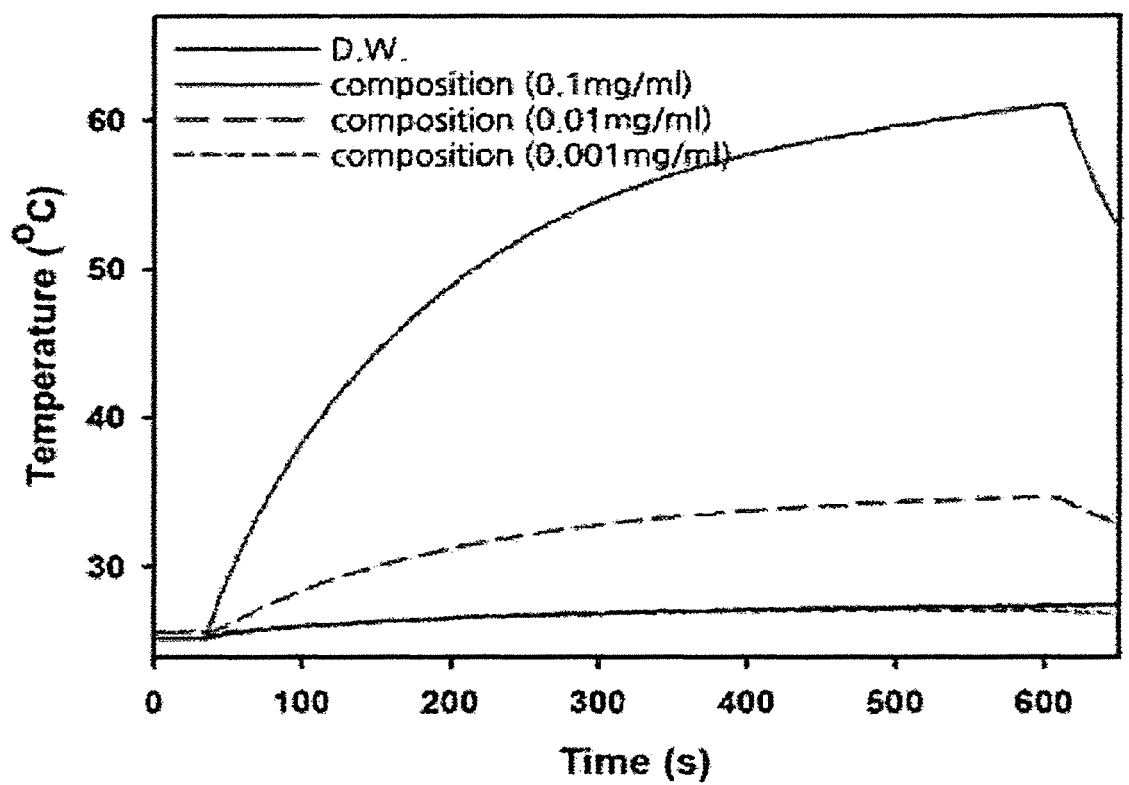
FIG. 1 is a graph illustrating a thermal energy emission behavior according to a concentration of dextran-coated SWNT according to Experimental Example 1.

Unless otherwise defined in the present specification, all technical and scientific terms used herein have the same meaning as commonly understood by those skilled in the art. Various scientific events, including the terms included in the present specification, are well known and available in the art. Although any methods and materials similar or equivalent to those described in the present specification are found to be used in the practice or testing of the present application, some methods and materials have been described. It should not be understood that the present invention is limited to specific methods, protocols and reagents because the present invention may be used in various ways depending on the context used by those skilled in the art.

As used in the present specification, the singular forms include plural objects unless the context clearly dictates otherwise. As used in the present specification, unless otherwise stated, "or" refers to "and/or". Moreover, other forms, for example, "have", "comprising" and "configuring" as well as the term "including" are not limited.

The numerical range includes numerical values defined in the above range. All maximum numerical limitations given throughout the present specification include all lower numerical limitations, as the lower numerical limitations are explicitly stated. All minimum numerical limitations given throughout the present specification include all higher numerical limitations, as the higher numerical limitations are explicitly stated. All numerical limitations given throughout the present specification will include any better numerical range within the broader numerical range, as narrower numerical limitations are explicitly stated. The titles provided in the present specification should not be understood as limiting the following exemplary embodiments as a reference of the specification in various aspects or on the whole.

The present invention provides a composition for target-specific photothermal therapy which has an effect on only cells to be treated without damaging other cells.

The term "photothermal therapy" used in the present specification means a therapy method of accumulating a material generating heat by absorbing light in a location requiring hyperthermal therapy and irradiating light. Most of light in the infrared area is used and caused by aspects such as tissue permeability.

The term "carbon nanotube" used in the present specification means a material which has a hexagonal honeycomb structure in which one carbon atom is sp2-bonded to three other carbon atoms and a diameter of several nanometers to tens micrometers. The carbon nanotubes have various types and are classified into single-walled carbon nanotube (SWNT) consisting of only one wall, double-walled carbon nanotube (DWNT) consisting of two walls, and multi-walled carbon nanotube (MWNT) consisting of two or more walls according to the number of walls which cover a longitudinal direction as an axis.

The term "dextran" used in the present specification means soluble polysaccharide consisting of glucoses. The dextran is produced from sucrose by the action of microorganisms such as *Leuconostoc mesenteroides* and used as a plasma expander. It is known that the dextran has a characteristic uptaken by reacting with an inflammatory cell scavenger receptor.

An exemplary embodiment of the present invention provides a composition for target-specific photothermal therapy, comprising: (a) carbon nanotubes; and (b) dextran coated on the surface of the carbon nanotubes.

According to the present invention, the composition for photothermal therapy is specific to inflammatory cells.

The term "target-specific" used in the present specification refers to a characteristic that the composition for photothermal therapy according to the present invention binds to the corresponding target or tissue in various kinds of targets or tissues present in a living body of the human or animals.

The term "inflammation" used in the present specification refers to a pathological condition of abscesses formed by invasion of external infectious sources (bacteria, fungi, viruses, various kinds of allergens). As a mechanism of inflammation, it is known that vasodilatation, increased capillary permeability, and aggregation of macrophages into inflamed areas are caused by the release of histamine and kinin due to cellular damage, and as a result, increased blood flow, swelling, migration of immune cells and antibodies, pain, fever, etc. occur at the infected areas.

The term "macrophage" used in the present specification refers to major cells responsible for innate immunity, and most of macrophages are fixed to the whole body, but some macrophages are present in a form of monocytes in the blood. The monocytes may be differentiated into dendritic cells or macrophages.

According to the present invention, the composition for photothermal therapy is used for diagnosis or treatment of inflammatory cell-mediated diseases.

The term "inflammatory cell-mediated disease" used in the present specification includes rheumatoid arthritis, ulcerative colitis, Crohn's disease, psoriasis, osteomyelitis, multiple sclerosis, atherosclerosis, pulmonary fibrosis, sarcoidosis (sarcomatosis), systemic sclerosis, graft versus host disease (GVHD) or chronic inflammation, but is not limited thereto.

The term "diagnosis" used in the present specification is to identify the presence or characteristic of a pathological condition and may include determining whether the corresponding subject has recurrence, metastasis, drug reactivity, resistance, etc. after treatment of the inflammatory cell-mediated disease as well as identifying whether the inflammatory cell-mediated disease occurs according to the present invention.

The term "treatment" used in the present specification refers to all activities in which symptoms of the inflammatory cell-mediated disease are improved or completely cured by the composition for photothermal therapy according to the present invention.

Another exemplary embodiment of the present invention provides a method of photothermal therapy for subjects except for the human, comprising: administering a composition for target-specific photothermal therapy according to the present invention; and percutaneously irradiating light having a wavelength of 600 to 1000 nm.

The term "subject" used in the present specification includes monkeys, dogs, goats, pigs or rats to which the composition for photothermal therapy according to the present invention is administered to improve the inflammatory cell mediated diseases, but is not limited thereto.

The term "administration" used in the present specification refers to providing a predetermined composition for photothermal therapy according to the present invention to the subject by any appropriate method. The administration includes both oral administration and parenteral administration, but the composition is preferably administered in a parenteral manner. The parenteral administration includes, for example, intravenous injection, subcutaneous injection, muscle injection, intraperitoneal injection, transdermal administration, or intralesional injection, but is not limited thereto. An appropriate does of the composition for photothermal therapy according to the present invention varies depending on factors such as a formulation method, an administration method, age, weight, gender, and pathosis of a patient, food, an administration time, an administration route, an excretion rate and response sensitivity, and usually, skilled doctors may easily determine and prescribe an effective dose for desired treatment or prevention.

According to the present invention, the light wavelength is in a range of 600 to 1000 nm. If the wavelength is less than 600 nm, the laser wavelength is short and does not penetrate deeply into the living tissue, and as a result, only photothermal treatment can be performed near the skin. If the wavelength is larger than 1000 nm, interference due to absorption of excess water existing in the living body increases, and thus, it is not preferable. The irradiation of the light may be performed percutaneously. Further, the irradiation of the light may be performed by a lamp or a laser.

According to the present invention, the composition for photothermal therapy comprising carbon nanotubes coated with dextran is absorbed only into desired target cells, i.e., inflammatory cells to cause thermotherapeutic action through light irradiated from an external light source, while not damaging cells except for inflammatory cells. Accordingly, the composition for photothermal therapy according to the present invention has advantages of minimizing side effects and maximizing therapeutic effects.

Hereinafter, various Examples are provided to help in understanding of the present invention. The following Examples are provided only for the purpose of easier understanding of the invention, but the scope of the present invention is not limited to the following Examples.

EXAMPLES

Example 1. Preparation of SWNT Coated with Dextran 40 to 80 mg of HiPCO as SWNT was dispersed in a 1% phenoxylated dextran (a molecular weight of dextran is 40 to 170 kDa) aqueous solution containing 14% phenoxy groups using a ultrasonic disperser (10 W, 1 hour), and then non-dispersed carbon nanotube bundles, catalysts, and the like were removed by using a bench top centrifuge (16,168 g) to prepare SWNT coated with dextran.

EXPERIMENTAL EXAMPLES

Experimental Example 1. Verification of Thermal Energy Emission Behavior According to Concentration of Dextran-Coated SWNT While light of an NIR laser (wavelength=808 nm) was irradiated to 0.1 mg/ml, 0.01 mg/ml and 0.001 mg/ml of the dextran-coated SWNT prepared in Example 1 for 10 minutes, respectively, changes in temperature were observed. The results were illustrated in FIG. 1.

Referring to FIG. 1, it was observed that while light energy was converted into thermal energy, the temperature was increased and it was verified that the temperature was decreased after the laser was turned off. As a result, it was verified that the dextran-coated SWNT prepared in Example 1 had an effect of photothermal therapy only when the NIR laser was irradiated. Also, the temperature was increased to a maximum of 60° C. at a concentration of 0.1 mg/ml, but the increased range of the temperature was less than 35° C. at a concentration of 0.01 mg/ml, and as a result, there was a difference in the maximum temperature range depending on the concentration.

Experimental Example 2. Verification of Cytotoxicity of Dextran-Coated SWNT

In order to determine cytotoxicity of the dextran-coated SWNT prepared in Example 1, an MTT assay to verify cell viability was performed.

Raw 264.7 was used as a cell line, the number of cells was determined by a hemocytometer, and then the same amount of cells was seeded in each well of a 96-well plate. The composition was treated in each well at concentrations of $10^{-8}$, $10^{-7}$, $10^{-6}$, $10^{-5}$, $10^{-4}$, $10^{-3}$, $10^{-2}$, $10^{-1}$, and 100 and cultured at 37° C. for 24 hours to induce uptake to cells. The supernatant of each well was removed and an MTT solution was added to the wells. The MTT solution was dissolved with 3-[4,5-dimethylthiazol-2-yl]-2,5-diphenyltetrazolium bromide (MTT) dissolved with 2 mg per PBS 1 ml, filtrated by a filter of 0.22 μm, stored in a 4° C. dark condition, and used. The cell line was cultured for 4 hours under a 37° C. dark condition after treatment of the MTT solution. Next, the supernatant was removed and DMSO was added, and after shaking for 10 minutes, the number of viable cells was measured at a wavelength of 540 nm using an ELISA device. As a control, the cell line was cultured in the same manner in the wells treated with only dextran at concentrations of $10^{-8}$, $10^{-7}$, $10^{-6}$, $10^{-5}$, $10^{-4}$, $10^{-3}$, $10^{-2}$, $10^{-1}$, and 100 and then the MTT assay was performed, and the results were illustrated in FIG. 2.

Figure 2:
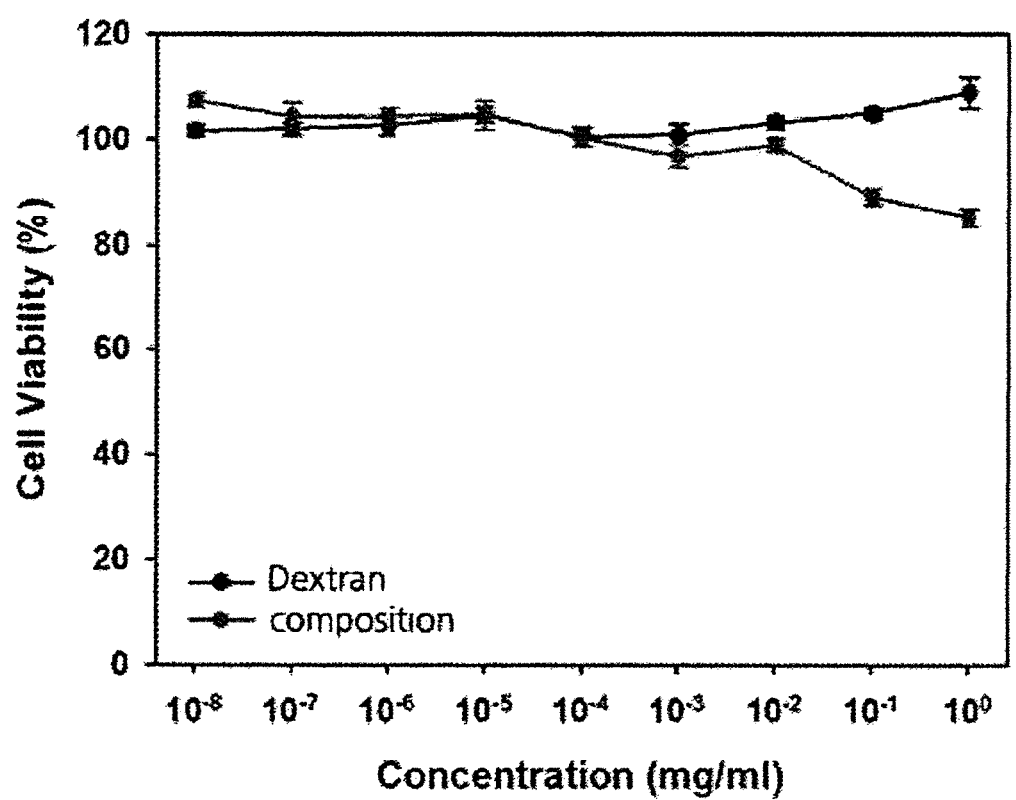
FIG. 2 is a graph illustrating verification of cytotoxicity of dextran-coated SWNT according to Experimental Example 2.

Referring to FIG. 2, as a control according to the present invention, even in a group treated with only dextran and a group treated with the dextran-coated SWNT according to the present invention, 80% or more of cell viability was shown. Accordingly, it was verified that the dextran-coated SWNT according to the present invention did not have cytotoxicity.

Figure 3:
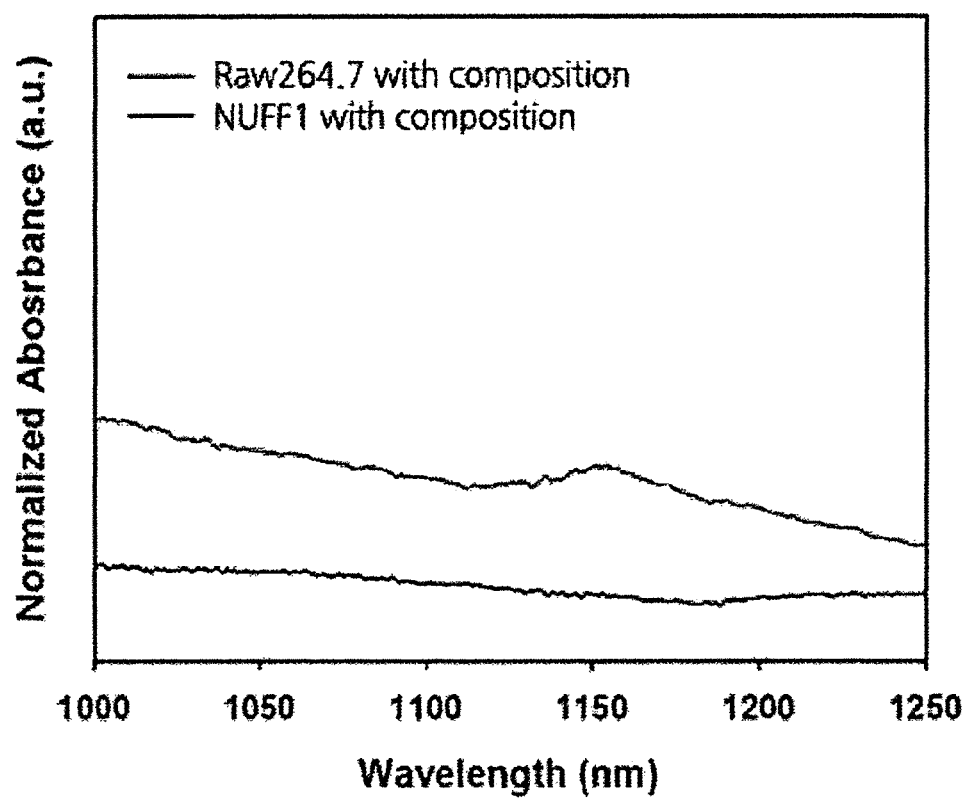
FIG. 3 is a graph illustrating comparison of UV absorbance for each cell line treated with dextran-coated SWNT according to Experimental Example 3.
Figure 4:
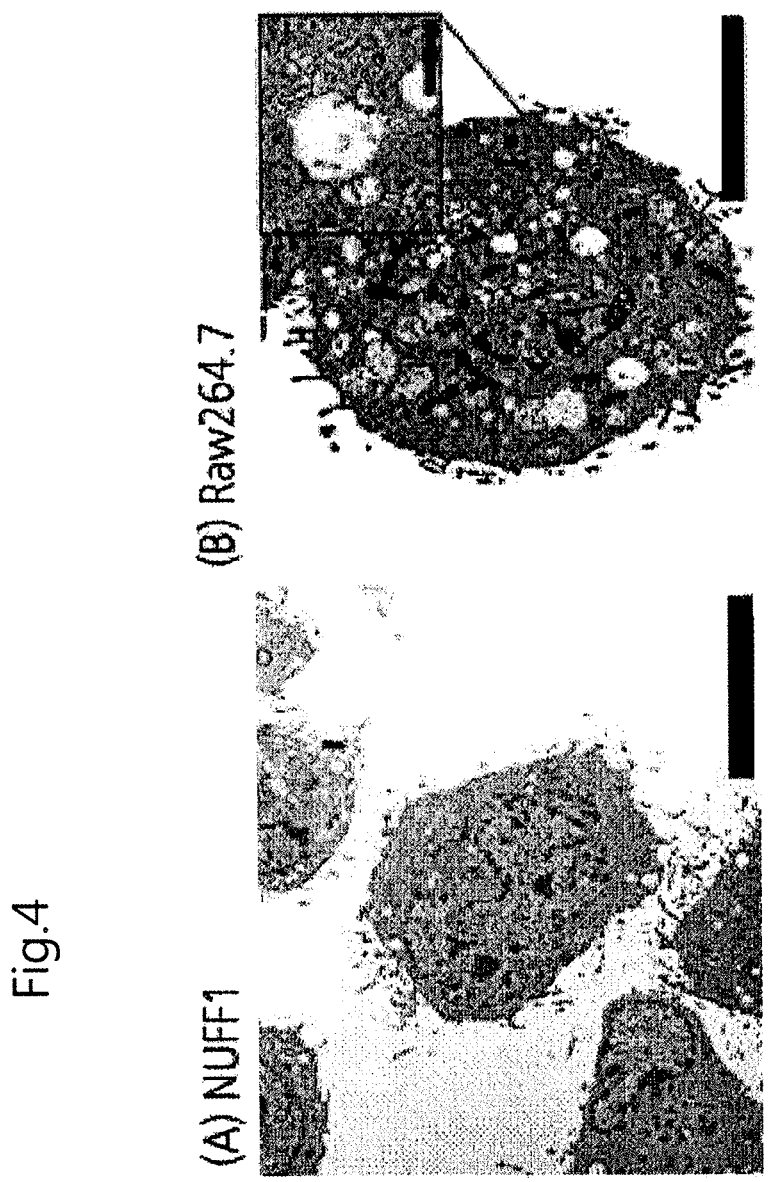
FIG. 4 illustrates a transmission electron microscope (TEM) photograph of a NUFF1 cell line (A) and a Raw264.7 cell line (B) treated with the dextran-coated SWNT according to Experimental Example 3.

Experimental Example 3. Verification of Target-Cell Specificity of Dextran-Coated SWNT (1) Verification of Cell Uptake of Dextran-Coated SWNT In order to verify whether the dextran-coated SWNT prepared by Example 1 has target specificity, the dextran-coated SWNT was treated to the cell line for 24 hours to induce uptake to cells. As the cell line, a human fibroblast cell line NUFF1 and a mouse macrophage cell line Raw264.7 were used, and after 24 hours of treatment, UV was irradiated. Through FIG. 3, it was verified that the dextran-coated SWNT had a peak difference depending on the cells. Also, through FIG. 4, it was verified that the dextran-coated SWNT was stably uptaken in the Raw264.7 cell line.

(2) Verification of Proper Concentration of Dextran-Coated SWNT

Serial dilution of the concentration of 0.1 mg/ml of the dextran-coated SWNT by ½ was performed in the Raw264.7 cell line for 24 hours and then the cell killing result by the NIR laser irradiation (wavelength: 808 nm) was verified. The results were illustrated in FIG. 5.

Figure 5:
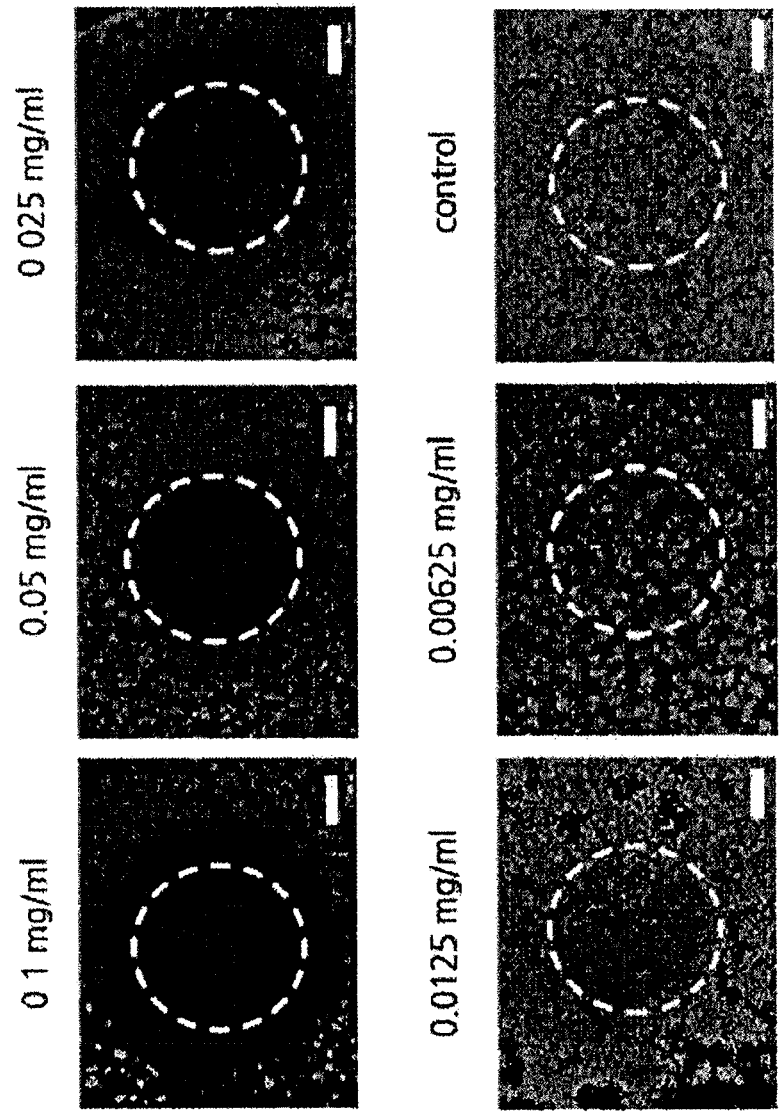
FIG. 5 illustrates results of comparing cell killing effects according to a concentration of the dextran-coated SWNT according to Experimental Example 3 under a condition of NIR laser irradiation of Experimental Example 3.

Referring to FIG. 5, in the group treated with the dextran-coated SWNT at a concentration of 0.1 mg/ml, cell death also occurred even in areas other than the area irradiated with the laser, but when the concentration of the dextran-coated SWNT of 0.05 mg/ml was treated, cell death occurred only in the area irradiated with the laser. On the other hand, when the concentration of the dextran-coated SWNT was less than 0.05 mg/ml, it was verified that the cell killing effect was weak.

Figure 6:
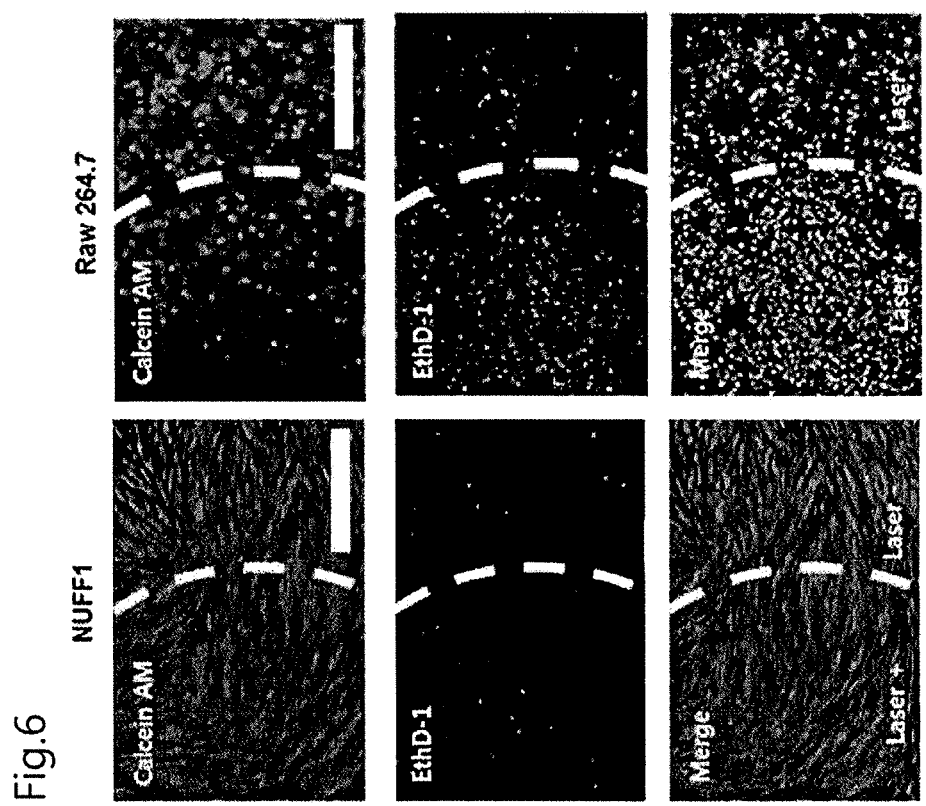
FIG. 6 illustrates results of comparing cell killing effects according to laser irradiation to the NUFF1 cell line and the Raw264.7 cell line treated with the dextran-coated SWNT according to Experimental Example 3.

(3) Verification of Target-Specific Cell Killing Effect of Dextran-Coated SWNT 0.05 mg/ml of the dextran-coated SWNT prepared by Example 1 was treated in Raw264.7 and NUFF1 for 24 hours and then irradiated with an NIR laser (wavelength: 808 nm). The laser-irradiated cells were stained with calcein AM, a dye that was colored by the enzymatic action of living cells, and EthD-1, a dye that was colored by binding to nucleic acid of dead cells with damaged cell membranes, and observed with a fluorescence microscope. The results were illustrated in FIG. 6. Referring to FIG. 6, it was verified that the NUFF1 was not affected by the laser irradiation treatment, but the Raw264.7, the target cells, had cell death in the laser irradiated area.

Figure 7:
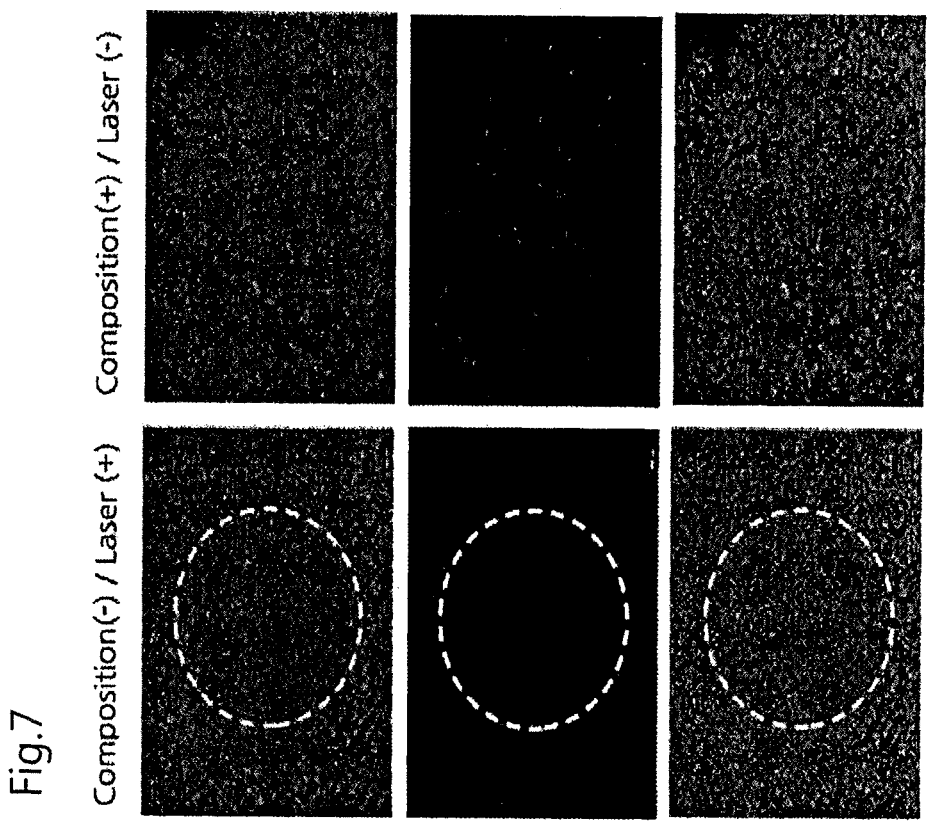
FIG. 7 illustrates results of NIR laser irradiation to the Raw264.7 cell line in the absence of the dextran-coated SWNT according to Experimental Example 3.

On the other hand, the result obtained when the Raw264.7 cell line was irradiated with only the NIR laser was compared with the result obtained when the Raw264.7 cell line treated with the dextran-coated SWNT was irradiated with the NIR laser irradiation. The results were illustrated in FIG. 7. Referring to FIG. 7, when the Raw264.7 cell line was irradiated with only the NIR laser, it was verified that the cell death did not occur.

For now, the present invention has been described with reference to the exemplary embodiments. It is understood to those skilled in the art that the present invention may be implemented as a modified form without departing from an essential characteristic of the present invention. Therefore, the disclosed exemplary embodiments should be considered from not a limitative viewpoint but an explanatory viewpoint. The scope of the present invention is described in not the above description but the appended claims, and it should be analyzed that all differences within the scope equivalent thereto are included in the present invention.

What is claimed is:

1. A method of photothermal therapy for subjects, comprising:
    administering a composition consisting of (a) carbon nanotubes; and (b) dextran coated on the surface of the carbon nanotubes for target-specific photothermal therapy; and irradiating light,
    wherein a target of the target-specific photothermal therapy is macrophage cells which induce chronic inflammation in the subject, and
    the composition is administered with an amount resulting in a concentration in the subject of 0.05 mg/ml.

2. The method of photothermal therapy of claim 1, wherein the light is a near infrared (NIR) laser having a wavelength of 600 to 1000 nm.

3. A method of photothermal therapy of claim 1, wherein the carbon nanotubes are single walled carbon nanotubes (SWNTs).

* * * * *